United States Patent
Butler et al.

[11] Patent Number: 6,073,628
[45] Date of Patent: *Jun. 13, 2000

[54] APPARATUS FOR INDUCTION OF INHALED PHARMACOLOGICAL AGENT BY A PEDIATRIC PATIENT

[75] Inventors: Bruce D. Butler; R. David Warters, both of Houston, Tex.

[73] Assignee: The Board of Regents of the University of Texas System, Austin, Tex.

[ * ] Notice: This patent is subject to a terminal disclaimer.

[21] Appl. No.: 09/156,811

[22] Filed: Sep. 18, 1998

Related U.S. Application Data

[62] Division of application No. 08/841,937, Apr. 8, 1997.

[51] Int. Cl.⁷ ................................................. A61M 16/10
[52] U.S. Cl. ................................ 128/203.12; 128/203.28
[58] Field of Search .................... 128/203.28, 203.12, 128/203.14, 200.23, 205.11, 205.24, 206.24

[56] References Cited

U.S. PATENT DOCUMENTS

| | | |
|---|---|---|
| 4,809,692 | 3/1989 | Nowacki et al. . |
| 4,832,015 | 5/1989 | Nowacki et al. . |
| 5,042,467 | 8/1991 | Foley . |
| 5,167,506 | 12/1992 | Kilis et al. . |
| 5,363,842 | 11/1994 | Mishelevich et al. . |
| 5,517,983 | 5/1996 | Deighan et al. . |
| 5,522,380 | 6/1996 | Dwork . |
| 5,613,489 | 3/1997 | Miller et al. . |
| 5,617,849 | 4/1997 | Springett et al. .................. 128/206.24 |

OTHER PUBLICATIONS

Advertisement for DHD Healthcare, Canasotoa New York, Introducing the ACE Aerosol Cloud Enhancer with exclusive, detachable mask, 1 page.

Advertisement for Clement Clark Incorporated, Columbus, Ohio, Press Release The Windmill Trainer Improves Asthma Care, and The Windmill Trainer Instructions, 2 pages.

*Primary Examiner*—Aaron J. Lewis
*Assistant Examiner*—Teena Mitchell
*Attorney, Agent, or Firm*—Duane, Morris & Heckscher LLP

[57] ABSTRACT

This invention relates to an apparatus for inducing a pediatric patient breathing gas through a face mask to inhale a fluid pharmacological agent. The apparatus comprises a fluid conduit through which fluid pharmacological agent may be inhaled, and a sensory patient stimulator coupled to said conduit and accuatable by inspiratory or expiratory flow through said conduit.

17 Claims, 3 Drawing Sheets

APPARATUS FOR INDUCTION OF INHALED PHARMACOLOGICAL AGENT BY A PEDIATRIC PATIENT

REFERENCE TO RELATED APPLICATIONS

This application is a divisional of application Ser. No. 08/841,937, filed on Apr. 8, 1997, which is incorporated herein by reference.

BACKGROUND OF THE INVENTION

1. Field of the Invention

This invention relates to an apparatus for inducing a pediatric patient to inhale a fluid pharmacological agent through a face mask. The apparatus comprises a fluid conduit through which fluid pharmacological agent may be inhaled, and a sensory patient stimulator coupled to said conduit and accuatable by inspiratory or expiratory flow through said conduit.

2. Description of the Prior Art

In the medical arts, it is customary to deliver pharmacological agents to a patient. For instance, it is common to induce anesthesia in patients prior to many surgical procedures. A common method of inducing anesthesia is through the inhalation of pharmacological fluids through a face mask. The delivery of pharmacological agents through a face mask to a pediatric patient, particularly to a preschool age child, is often difficult. This difficulty is a result of many factors, including but not limited to a child's short attention span, fear, and/or an inability to comprehend the importance of inhaling pharmacological fluids.

The lack of cooperation exhibited by many pediatric patients during the course of attempting to administer pharmacological agents in fluid form can result in increased anxiety on the part of the patient, the patient's parents or guardians, and the anesthetist. There is also a risk of bodily injury to an uncooperative or combative patient. Such increased anxiety and lack of cooperation result in an increase in the time required to induce anesthesia in an uncooperative pediatric patient.

Common prior art procedures for inducing a pediatric patient to inhale pharmacological fluids for anesthesia are to allow the patient to first play with a face mask prior to the induction of pharmacological gas, so that the child becomes familiar and comfortable with mask ventilation.

The process of administering a fluid pharmacological agent comprises both inhalation or inspiration and exhalation or expiration by the patient. It is desirable to motivate the pediatric patient to maximize his breathing rate and volume of inhaled or inspired gases. The present invention provides an apparatus for inducing a pediatric patient to inhale pharmacological agent by providing a sensory stimulus to the pediatric patient which induces the patient to maximize his inhalation of a pharmacological agent. An advantage of the present invention is the potential for decreased dosage or necessity of preoperative sedation.

The sensory stimulus provided by the present invention is simple and inexpensive, requiring no electrical or electronic parts. This is one major advantage of the present invention over the inhaler devices of the prior art which involve complex and expensive electronics. Such prior art devices are disclosed in U.S. Pat. No. 5,363,842 to Mishelvich et al. and U.S. Pat. No. 5,167,506 to Kilis et al. Certain of these prior art devices, such as that disclosed in U.S. Pat. No. 5,167,506, use display screens which display text messages. Such text message screens are of little or no value with pediatric patients who have not yet learned to read.

Another advantage of the present invention is that the sensory stimulus is easily visible to a pediatric patient breathing gas through a face mask. Prior art inhalation devices comprise indicator means that are visible to a party dispensing drugs to a patient, but which provide insufficient visual or sensory stimulus to directly induce the patient to maximize his breathing. One such prior art device is disclosed in U.S. Pat. No. 4,832,015 to Nowacki et al.

SUMMARY OF THE INVENTION

The present invention is directed toward an apparatus for inducing a pediatric patent to inhale a fluid pharmacological agent through a face mask. The invention comprises a fluid conduit having a first end and second end. The first end is capable of being coupled to a source of fluid pharmacological agent and the second end is capable of being coupled to a face mask sized to fit a pediatric patient such that fluid pharmacological agent flowing through the conduit can enter the face mask. The conduit has sufficient diameter to allow fluid pharmacological agent to flow through the conduit at a sufficient flow rate to be inhaled by a pediatric patient.

The invention further comprises a sensory patient stimulator coupled to the conduit such that the inspiratory or expiratory flow through the conduit activates the stimulator. The stimulator is positioned such that when it is activated, it can be seen by a pediatric patient breathing gas through a face mask connected to the second end of the conduit. The activation of the stimulator may be dynamic, such as by visible movement, or the activation may be static, such as by a visible color change.

DESCRIPTION OF THE PREFERRED EMBODIMENTS

The invention comprises a fluid conduit 10 having a first end 11 and a second end 12. The first end is capable of being coupled to a source of fluid pharmacological agent. The second end is capable of being coupled to a face mask sized to fit a pediatric patient, such that fluid pharmacological agent flowing through the conduit can enter a face mask. The conduit has a sufficient diameter to allow fluid pharmacological agent to flow through it at a sufficient flow rate to be inhaled by a pediatric patent.

Figure 4:
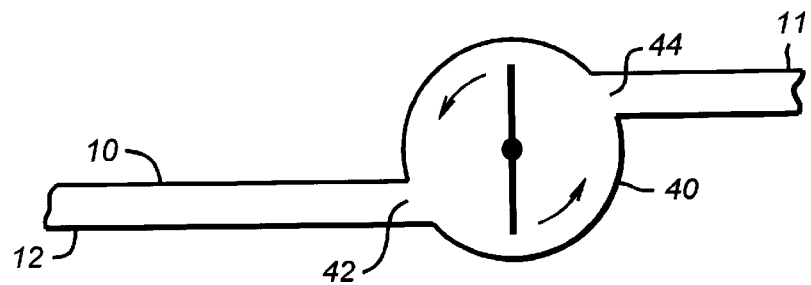
FIG. 4 is a top view of a fourth embodiment of the fluid conduit of the present invention.

In another embodiment, as shown in FIG. 4, the fluid conduit comprises a rotor housing 40 comprising a first port 44 and a second port 42. The first and second ports are positioned on opposite sides of the rotor housing and are offset from the center of the rotor housing. This offset provides unidirectional rotation of a rotor in said housing. In the embodiments shown in FIGS. 1, 2, 4, and 5, any ports or openings on the surface of the conduit allow communication with a closed volume, such as a visual stimulator housing. In these embodiments the conduit has no ports in communication with the ambient environment.

The invention further comprises a sensory patient stimulator 14, coupled to the conduit such that inspiratory or expiratory flow through the conduit activates the stimulator. The stimulator is positioned such that when it is activated, it provides a stimulus that is visible to a pediatric patient breathing gas through a face mask connected to the second end of the conduit.

Figure 1:
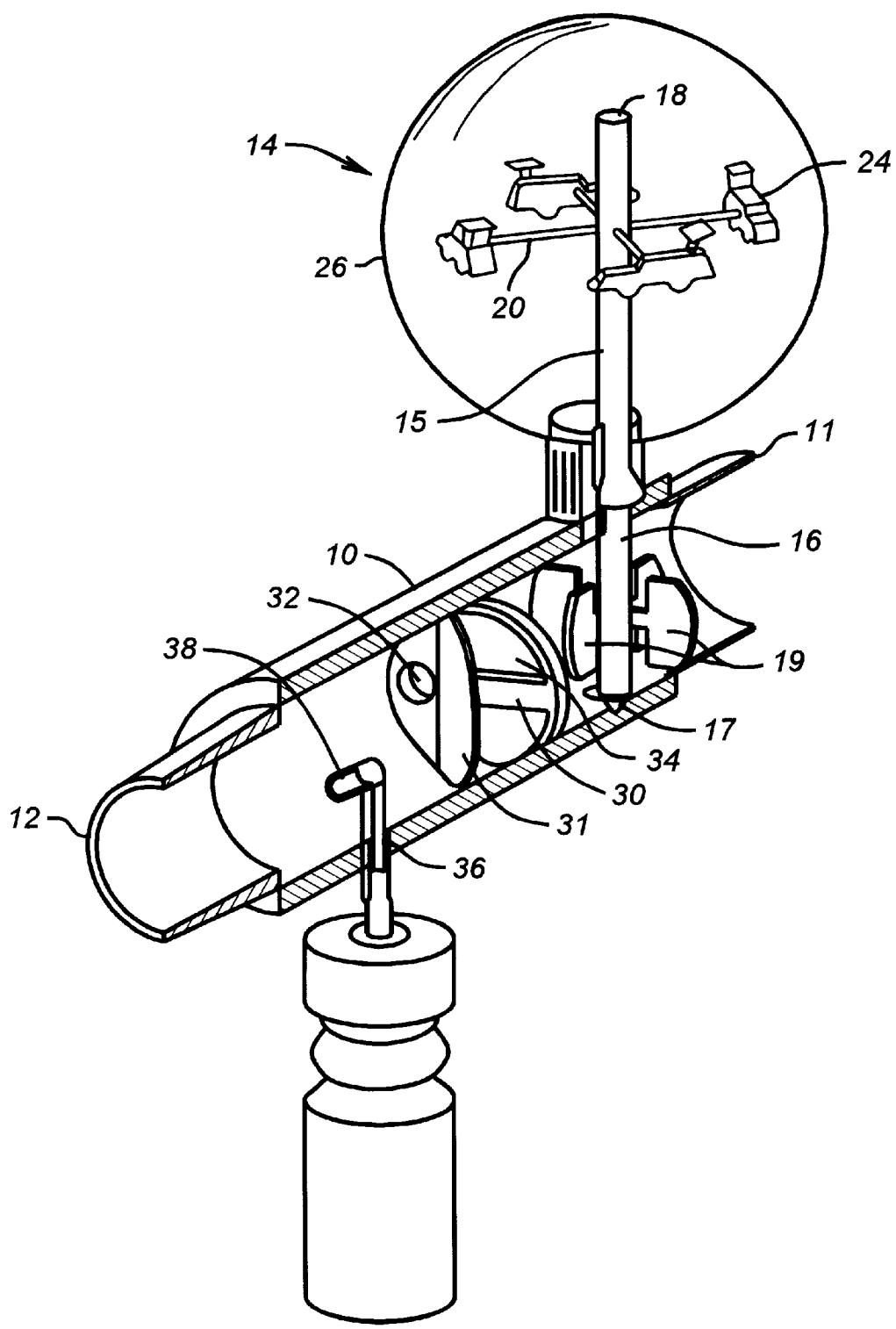
FIG. 1 is an isometric view of a first embodiment of the present invention.
Figure 2:
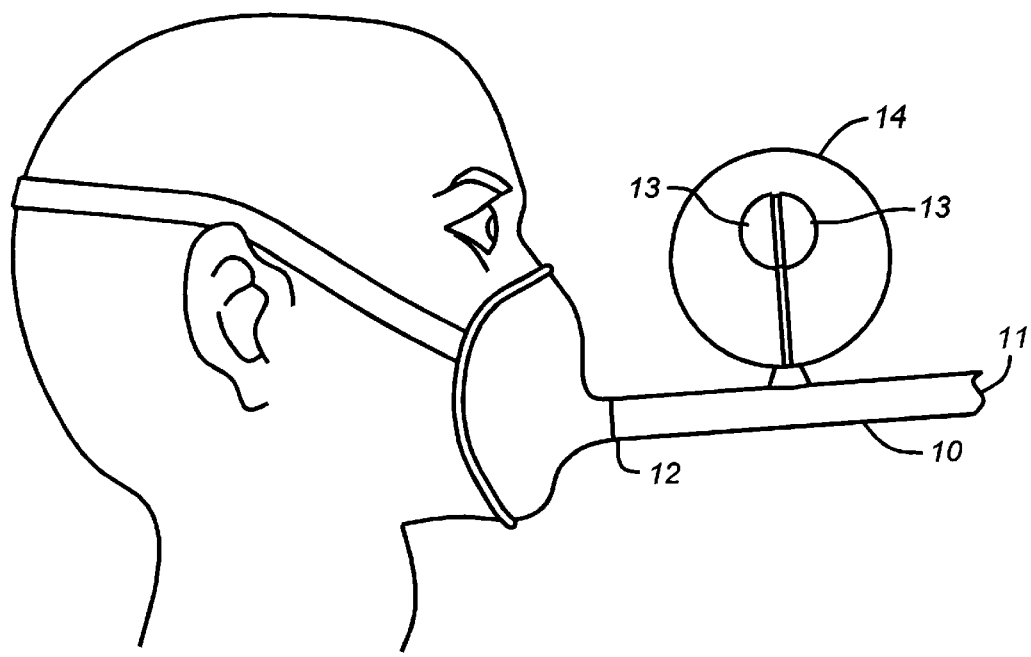
FIG. 2 is a side view of a second embodiment of the present invention being used by a pediatric patient.

In one preferred embodiment, the sensory patient stimulator 14 is a rotating visual stimulator as shown in FIGS. 1 and 2. The visual stimulator may comprise arcuate members 13, as shown in FIG. 2. In this embodiment, the stimulator may comprise a rotatable turbine 15 whose rotation is accuatable upon the patient's exhalation or inhalation, as shown in FIGS. 1 and 2.

Figure 6:
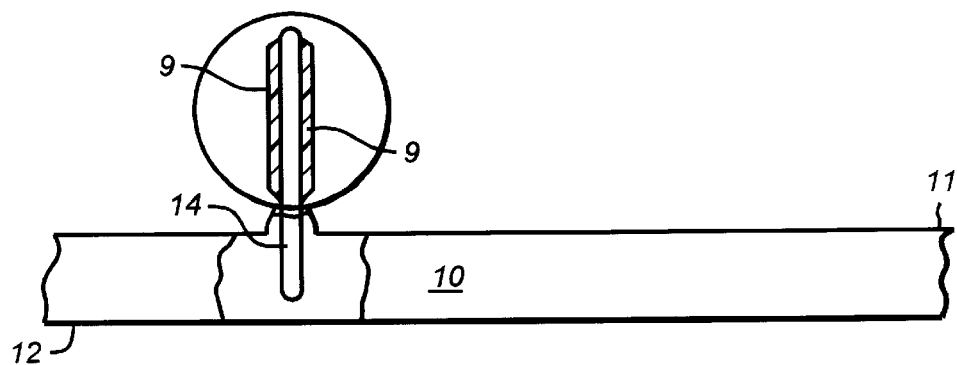
FIG. 6 is a side view of a sixth embodiment of the present invention.

In another preferred embodiment, the stimulator comprise a material that changes color in response to temperature changes as shown in FIG. 6. In this embodiment, the portion of the stimulator not positioned in the fluid conduit may be coated with a thermal liquid crystal paint 9 that changes color in response to temperature changes. Such paints are available from Cole-Parmer® Instrument Company. The inspiration and expiration of a pediatric patient through the fluid conduit cause air temperature changes which result in a visible color change in the stimulator.

In another preferred embodiment, the rotatable turbine comprises a turbine driven rotor 16 having a first end 17 in said fluid conduit, a second end 18 extending outside said fluid conduit, and at least two turbine blades 19 affixed to the first end. As shown in FIG. 1, the turbine blades are positioned in the stream of ventilatory gases. In this embodiment, the second end of the rotor comprises at least one arm 20 extending radially outward, such that when the rotor rotates, the rotation of the arm is visible to a patient inhaling or exhaling ventilatory gases through a face mask. The visual stimulation may also comprise a spherical element located on the second end of said rotor.

The arm comprises a near end 21 attached to the rotor, a far end 22 opposite the near end, and a visual object 24 affixed to the far end. In a preferred embodiment, each of the visual objects is of sufficient size to capture the attention of the patient inhaling or exhaling ventilatory gases through a face mask when the rotor is rotating, as depicted in FIGS. 1 and 2. In preferred embodiments, the visual object may be shaped to represent things that young children readily associate with motion, such as a car, truck or an animal.

Figure 3:
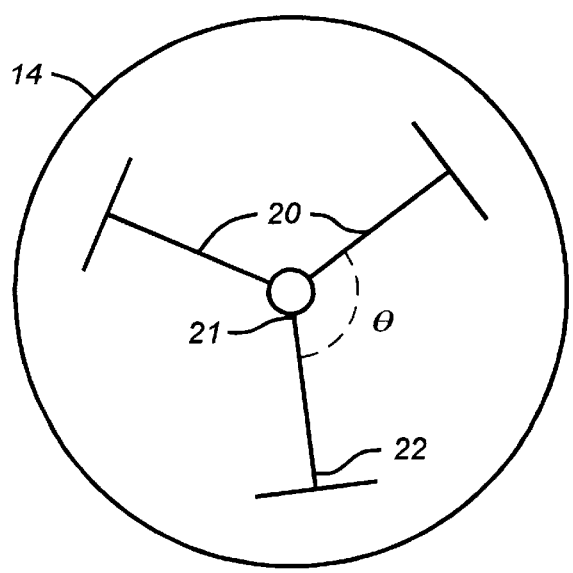
FIG. 3 is a top view of a third embodiment of the rotor and arm assembly of the present invention.

In one embodiment of the present invention, the rotor comprises at least three arms spaced apart radially by at least 90°, as shown in FIG. 3. In FIG. 3, the spacing angle between adjacent arms is denoted by the symbol θ.

In another embodiment of the present invention, the rotor comprises four arms spaced apart radially by at least 60°, as shown in FIG. 1. In a preferred embodiment, the second end of the rotor and the arms are housed within a transparent housing 26, as shown in FIG. 1.

In another embodiment of the present invention, a flow control device 30 is installed in the conduit. In a preferred embodiment, the flow control device comprises a check valve 31. The check valve may be a flapper valve, as shown in FIG. 1.

Figure 5:
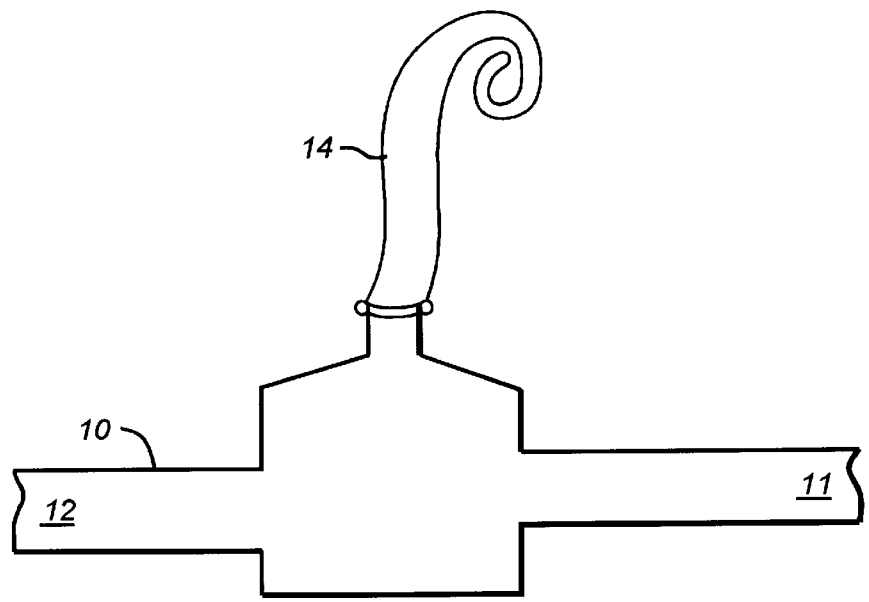
FIG. 5 is a side view of a fifth embodiment of the present invention.

In another preferred embodiment, the visual stimulator 14 is inflatable in response to a patients' exhalation and deflatable in response to a patient's inhalation, as shown in FIG. 5.

In another preferred embodiment, the flow control device comprises an inhalation port 34, an exhalation port 32, and a check valve, as shown In FIG. 1. In a preferred embodiment, the exhalation port and inhalation port are positioned on the flow control device to produce rotation of the turbine driven rotor in the same direction upon the patient's inhalation and exhalation.

In a preferred embodiment, the invention further comprises a fluid injection port 36 positioned in the fluid conduit between the second end of the fluid conduit and the flow control device. In a preferred embodiment, the invention further comprises a flow diverter 38 positioned in the fluid conduit, such that fluid injected into the fluid injection port is directed toward the second end of the fluid conduit.

The foregoing disclosure and description of the invention are illustrative and explanatory thereof, and various changes in the size, shape and materials, as well as in the details of the illustrated construction, may be made without departing from the spirit of the invention.

What is claimed is:

1. An apparatus for inducing a pediatric patient to inhale a fluid pharmacological agent through a face mask, comprising:

a. a fluid conduit having a first end and a second end, said first end capable of being coupled to a source of fluid pharmacological agent and said second end capable of being coupled to a face mask sized to fit a pediatric patient such that fluid pharmacological agent flowing through said conduit can enter a face mask, said conduit having sufficient diameter to allow fluid pharmacological agent to flow through said conduit at a sufficient flow rate to be inhaled by a pediatric patient; and b. a sensory patient stimulator coupled to said conduit, said stimulator comprising a rotatable turbine whose rotation is actuatable by a pediatric patient's exhalation or inhalation, said stimulator being positioned such that when it is activated, it provides a stimulus that is visible to a pediatric patient breathing through a face mask connected to said second end of said conduit.

2. The apparatus of claim 1, further comprising a flow control device installed in said conduit.

3. The apparatus of claim 2, wherein said flow control device comprise a check valve.

4. The apparatus of claim 3, wherein said check valve is a flapper valve.

5. The apparatus of claim 2, wherein said rotatable turbine comprises a turbine driven rotor comprising a first end in said fluid conduit, a second end extending outside said fluid conduit and at least two turbine blades affixed to said first end.

6. The apparatus of claim 5, wherein said second end of said rotor comprises at least one arm extending radially outward, such that when said rotor rotates, the rotation of said arm is visible to a pediatric patient inhaling or exhaling ventilatory gases through a face mask.

7. The apparatus of claim 6, wherein each of said arms comprises a near end attached to said rotor, a far end opposite said near end, and a visual object affixed to said far end.

8. The apparatus of claim 7, wherein each of said visual objects is of sufficient size to capture the attention of a pediatric patient inhaling or exhaling ventilatory gases through a face mask, when said rotor is rotating.

9. The apparatus of claim 8, wherein said second end of said rotor comprises at least two arms spaced apart radially by at least 150 degrees.

10. The apparatus of claim 8, wherein said second end of said rotor and said arms are housed within a transparent housing.

11. An apparatus for inducing a pediatric patient to inhale a fluid pharmacological agent through a face mask, comprising:

a. a fluid conduit having a first end, a second end, and no ports in communication with the ambient environment, said first end capable of being coupled to a source of fluid pharmacological agent and said second end capable of being coupled to a face mask sized to fit a pediatric patient such that fluid pharmacological agent flowing through said conduit can enter a face mask, said conduit having sufficient diameter to allow fluid pharmacological agent to flow through said conduit at a sufficient flow rate to be inhaled by a pediatric patient; and b. a visual patient stimulator coupled to said conduit such that inspiratory or expiratory flow through said conduit activates said stimulator, said stimulator being positioned such that when it is activated, it can be seen by a pediatric patient breathing gas through a face mask connected to said second end of said conduit.

12. The apparatus of claim 11, wherein said stimulator comprises a turbine driven rotor comprising a first end in said fluid conduit, a second end extending outside said fluid conduit, and at least two turbine blades affixed to the first end and wherein the second end of said rotor comprises at least one arm extending radially outward such that when said rotor rotates, the rotation of said arm is visible to a patient breathing the ventilatory gases through a face mask.

13. The apparatus of claim 12, further comprising a flow control device installed in said conduit, said flow control device comprising an inhalation port, an exhalation port and a check valve.

14. The apparatus of claim 13, further comprising a fluid injection port positioned in said fluid conduit between said second end of said fluid conduit and said flow control device.

15. The apparatus of claim 14, further comprising a flow diverter positioned in said fluid conduit such that fluid injected into said fluid injection port is directed toward said second end of said fluid conduit.

16. The apparatus of claim 11, wherein said stimulator is inflatable in response to a patient's exhalation and deflatable in response to a patient's inhalation.

17. The apparatus of claim 11, wherein said stimulator comprises a material that changes color in response to temperature changes.

* * * * *